United States Patent [19]

Schinski et al.

[11] 4,260,410
[45] Apr. 7, 1981

[54] HERBICIDAL AND PLANT-GROWTH-REGULATING N-HALOACETYLPHENYLAMINO CARBONYL OXIMES

[75] Inventors: William L. Schinski, San Rafael; David C. K. Chan, Petaluma; Irene C. Huang, Huntington Beach, all of Calif.

[73] Assignee: Chevron Research Company, San Francisco, Calif.

[21] Appl. No.: 14,410

[22] Filed: Feb. 23, 1979

Related U.S. Application Data

[63] Continuation-in-part of Ser. No. 892,365, Mar. 31, 1978, Pat. No. 4,174,210.

[51] Int. Cl.$^3$ ............ A01N 37/22; C07C 131/00; C07C 103/375
[52] U.S. Cl. ............................. 71/76; 71/78; 71/88; 71/90; 71/94; 71/95; 71/98; 71/118; 260/326.16; 260/345.7 R; 260/347.3; 260/454; 260/465 D; 546/216; 546/222; 546/224; 546/221; 546/292; 546/297; 546/308; 549/28; 549/69; 549/63; 564/211; 564/214
[58] Field of Search ............... 260/562 B, 454, 465 D; 71/118, 76, 98

[56] References Cited

U.S. PATENT DOCUMENTS

| | | | |
|---|---|---|---|
| 3,429,690 | 2/1969 | Olin | 71/118 |
| 3,483,231 | 12/1969 | Marcus et al. | 71/121 |
| 3,624,151 | 11/1971 | Gutman | 260/557 R |
| 3,769,301 | 10/1973 | Olin | 71/118 |
| 3,847,590 | 11/1974 | Hubele | 71/121 |
| 3,903,162 | 9/1975 | Chupp | 260/562 B |
| 3,942,972 | 3/1976 | Richter et al. | 71/88 |
| 3,966,811 | 6/1976 | Krenzer | 260/562 B |
| 3,976,471 | 8/1976 | Richter et al. | 71/118 |
| 3,983,174 | 9/1976 | Richter et al. | 260/562 B |
| 4,008,066 | 2/1977 | Moser | 71/76 |
| 4,052,194 | 10/1977 | Wilcox | 71/121 |
| 4,126,440 | 11/1978 | Moser | 71/76 |

FOREIGN PATENT DOCUMENTS

| | | | |
|---|---|---|---|
| 758308 | 4/1971 | Belgium | 71/118 |
| 768977 | 12/1971 | Belgium | 71/118 |
| 51 | 12/1978 | European Pat. Off. | 71/118 |
| 2402983 | 8/1974 | Fed. Rep. of Germany | 71/118 |

*Primary Examiner*—Donald G. Daus
*Assistant Examiner*—Diana G. Rivers
*Attorney, Agent, or Firm*—D. A. Newell; T. G. DeJanghe; R. J. Suyat

[57] ABSTRACT

Novel N-haloacetylphenylamino carbonyl oximes represented by the formula

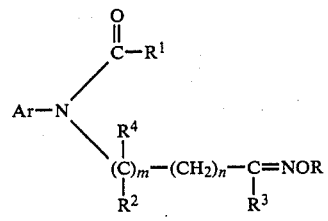

wherein Ar is phenyl or substituted phenyl; $R^1$ is halomethyl; $R^2$ and $R^3$ are each independently hydrogen, alkyl, phenyl, benzyl, substituted phenyl or benzyl, haloalkyl, cyanoalkyl, alkoxyalkyl, alkylthioalkyl or thiocyanoalkyl; $R^4$ is hydrogen or alkyl; n is 0 or 1; m is 0 or 1; R is hydrogen, alkyl, alkenyl, alkynyl, alkylthioalkyl, haloalkyl, alkoxyalkyl, cyanoalkyl, phenyl, benzyl, substituted phenyl or benzyl, or R is acyl of the formula

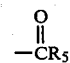

wherein $R^5$ is hydrogen, alkyl, haloalkyl, alkoxyalkyl, alkylthioalkyl, alkoxy, alkylthio, acetonyl, or the group -NR'R" wherein R' and R" are independently hydrogen, alkyl or phenyl; with the proviso that $R^2$ and $R^3$ may be joined together to form a carbocyclic ring or a heterocyclic ring; or R and $R^2$ may be joined together to form a heterocyclic ring; or R and $R^3$ may be joined together to form a heterocyclic ring.

21 Claims, No Drawings

HERBICIDAL AND PLANT-GROWTH-REGULATING N-HALOACETYLPHENYLAMINO CARBONYL OXIMES

RELATED APPLICATION

This application is a continuation-in-part of application Ser. No. 892,365, filed Mar. 31, 1978 now U.S. Pat. No. 4,174,210.

DESCRIPTION OF THE PRIOR ART

U.S. Pat. No. 3,976,471, issued on Aug. 24, 1976, to S. B. Richter discloses herbicidal N-(alkylideneaminooxymethyl)-alpha-haloacetanilides.

U.S. Pat. No. 3,966,811, issued on June 29, 1976, to J. Krenzer, discloses herbicidal dialkylacetals of anilinoacetaldehydes.

DESCRIPTION OF THE INVENTION

The compounds of the invention are represented by the formula

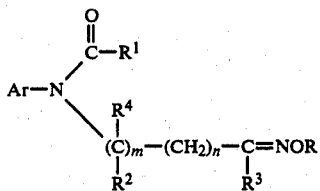

wherein Ar is phenyl or phenyl substituted with 1 to 4 of the same or different substituents selected from fluoro, chloro, bromo, iodo, or alkyl of 1 to 4 carbon atoms, or substituted with 1 to 2 of the same or different substituents selected from alkoxy of 1 to 4 carbon atoms, nitro or haloalkyl of 1 to 2 carbon atoms and 1 to 3 of the same or different halogens selected from fluoro, chloro, bromo or iodo;

$R^1$ is halomethyl of 1 to 3 of the same or different halogens selected from fluoro, chloro, bromo or iodo;

$R^2$ and $R^3$ are each independently hydrogen, alkyl of 1 to 6 carbon atoms, phenyl, benzyl, phenyl or benzyl substituted with 1 to 2 of the same or different substituents selected from fluoro, chloro, bromo, iodo, alkyl of 1 to 4 carbon atoms, alkoxy of 1 to 4 carbon atoms or nitro; haloalkyl of 1 to 4 carbon atoms and 1 to 10 of the same or different halogens selected from fluoro, chloro, bromo or iodo, cyanoalkyl of 2 to 6 carbon atoms, alkoxyalkyl of 2 to 6 carbon atoms, alkylthioalkyl of 2 to 6 carbon atoms, or thiocyanoalkyl of 2 to 6 carbon atoms;

$R^4$ is hydrogen or alkyl of 1 to 6 carbon atoms;

n is 0 or 1;

m is 0 or 1;

R is hydrogen, alkyl of 1 to 6 carbon atoms, alkenyl of 3 to 6 carbon atoms, alkynyl of 3 to 6 carbon atoms; alkylthio of 2 to 6 carbon atoms, haloalkyl of 1 to 4 carbon atoms and 1 to 10 of the same or different halogens selected from fluoro, chloro, bromo or iodo, alkoxyalkyl of 2 to 6 carbon atoms, cyanoalkyl of 2 to 6 carbon atoms, phenyl, benzyl, phenyl or benzyl substituted with 1 to 2 of the same or different substituents selected from fluoro, chloro, bromo, iodo, alkyl of 1 to 4 carbon atoms, alkoxy of 1 to 4 carbon atoms or nitro, or R is acyl of the formula

wherein $R^5$ is hydrogen, alkyl of 1 to 4 carbon atoms, haloalkyl of 1 to 4 carbon atoms and 1 to 10 of the same or different halogens selected from fluoro, bromo, chloro or iodo, alkoxyalkyl of 2 to 6 carbon atoms, alkylthioalkyl of 2 to 6 carbon atoms, alkoxy of 1 to 6 carbon atoms, alkylthio of 1 to 6 carbon atoms, acetonyl, or the group -NR'R" wherein R' and R" are independently hydrogen, alkyl of 1 to 6 carbon atoms or phenyl;

with the proviso that $R^2$ and $R^3$ may be joined together to form a carbocyclic ring of 5 to 6 carbon atoms or a heterocyclic ring containing one O, N or S hetero atom and 4 to 5 carbon atoms; or R and $R^2$ may be joined together to form a heterocyclic ring containing 3 or 4 carbon atoms; or R and $R^3$ may be joined together to form a heterocyclic ring containing 3 or 4 carbon atoms.

Representative Ar groups include 2-fluorophenyl, 2-chlorophenyl, 2,3-dichlorophenyl, 2-trifluoromethylphenyl, 3-bromophenyl, 3,5-diiodophenyl, 2-methylphenyl, 2-methyl-3-chlorophenyl, 2,3-dimethylphenyl, 2,3,5,6-tetramethylphenyl, 2,6-diethylphenyl, 2-methyl-6-ethylphenyl, 2,3,6-trimethylphenyl, 3,5-dimethylphenyl, 2-nitrophenyl and 2-ethoxyphenyl. The substituents on the phenyl ring are preferably in the 2-, 3-, 5- and 6-positions, and most preferably are in the 2- and 6-positions.

Representative $R^1$ groups include fluoromethyl, chloromethyl, bromomethyl, iodomethyl, dichloromethyl, tribromomethyl and fluorodichloromethyl.

Representative alkyl R, $R^2$ and $R^3$ are methyl, ethyl, isopropyl and n-hexyl.

Representative alkenyl R groups are allyl, 2-butenyl and 3-hexenyl. Representative alkynyl R groups are propargyl, 3-butynyl and 2-pentynyl. Representative substituted-phenyl R, $R^2$ and $R^3$ groups include 3-fluorophenyl, 2-chlorophenyl, 4-bromophenyl, 2-iodophenyl, 3-methylphenyl, 2,4-diethylphenyl, 3-methoxyphenyl and 2-nitrophenyl. Representative substituted-benzyl R, $R^2$ and $R^3$ groups include 4-chlorobenzyl, 2-methoxybenzyl, 2,4-dimethylbenzyl, 3-nitrobenzyl, etc.

Representative R, $R^2$, $R^3$ and $R^5$ haloalkyl groups include trichloromethyl, 1,1,2,2-tetrachloroethyl and fluoromethyl. Representative R, $R^2$ and $R^3$ cyanoalkyl groups include cyanomethyl and cyanoethyl. Representative R, $R^2$, $R^3$ and $R^5$ alkoxyalkyl groups include methoxymethyl, ethoxymethyl and methoxyethyl. Representative R, $R^2$, $R_3$ and $R^5$ alkylthioalkyl groups include methylthiomethyl, ethylthiomethyl and methylthioethyl. Representative $R^2$ and $R^3$ thiocyanoalkyl groups include thiocyanomethyl and thiocyanoethyl.

Preferred substituted phenol R, $R^2$ and $R^3$ groups are phenyl substituted with 1 to 2 fluoro, chloro, bromo or alkyl of 1 to 4 carbon atoms.

Representative groups in which $R^2$ and $R^3$ are joined together to form part of a ring include dimethylene, trimethylene, tetramethylene, —CH$_2$OCH$_2$—, —CH$_2$=N—CH$_2$—, —CH$_2$SCH$_2$—, —CH$_2$CH$_2$OCH$_2$—, —CH$_2$NHCH$_2$—, etc.

Representative $R^5$ groups include hydrogen, methyl, ethyl, isopropyl, trichloromethyl, fluoromethyl, methoxymethyl, methylthiomethyl, methoxy, ethoxy, methylthio, ethylthio, amino, methylamino, dimethylamino and anilino.

Representative $R^4$ groups include hydrogen, methyl and ethyl. Preferably $R^4$ is hydrogen.

Representative groups in which R and $R^2$ are joined include —$CH_2$— and —$CH_2CH_2$—.

Representative groups in which R and $R^3$ are joined include —$CH_2CH_2$— and —$CH_2CH_2CH_2$—.

Preferably $m=1$ when $n=0$ and $m=0$ when $n=1$.

Preferably Ar is phenyl substituted with 2 to 3 alkyl of 1 to 4 carbon atoms. Most preferably Ar is 2,6-dialkylphenyl, especially 2,6-dimethylphenyl and 2,6-diethylphenyl.

Preferably $R^1$ is monohalomethyl, especially chloromethyl or bromomethyl.

Preferably $R^2$ and $R^3$ individually are hydrogen or alkyl of 1 to 3 carbon atoms or are joined together to form part of a 5- or 6-membered carbocyclic ring, that is, $R^2$ and $R^3$ are dimethylene, trimethylene or tetramethylene.

Preferably R is hydrogen or alkyl of 1 to 6 carbon atoms. Most preferably R is alkyl of 1 to 3 carbon atoms.

When $m=0$ and $n=1$, R and $R^3$ are both preferably alkyl of 1 to 3 carbon atoms, most preferably methyl.

The oxime compounds of the invention are prepared by reaction of the carbonyl compound (III) and an alkoxyamino compound (III) by conventional procedures, as depicted in reaction (1):

$$\text{Ar-N} \begin{matrix} \overset{O}{\underset{\|}{C}}-R^1 \\ \underset{R^4}{|} \\ (C)_m-(CH_2)_n-\underset{R^3}{\underset{|}{C}}=O \end{matrix} + NH_2OR \longrightarrow (I) \quad (1)$$

(II)                                                    (III)

wherein R, $R^1$, $R^2$, $R^3$, $R^4$, n and m have the same meaning as previously defined.

Reaction (1) is generally conducted by reacting substantially equimolar amounts of the carbonyl compound (II) and the alkoxyamino compound (III) in the liquid phase in an inert diluent at a temperature of 0° to 100° C. Generally, the alkoxyamino compound is generated in situ from the corresponding alkoxyamino hydrochloride salt, e.g., hydroxylamine hydrochloride or methoxyamine hydrochloride, and a base, e.g., an inorganic alkali metal carbonate such as potassium carbonate or a trialkyl amine such as triethylamine.

The N-haloacetylanilino-substituted carbonyl compound (II) is generally prepared by acylating the anilino-substituted carbonyl compound with the haloacetyl halide as depicted in reaction (2):

$$\text{ArNH}(\underset{R^2}{\underset{|}{C}})_m(CH_2)_n\underset{R^3}{\underset{|}{C}}=O + X-\overset{O}{\underset{\|}{C}}-R^1 \longrightarrow (II) + HX \quad (2)$$

(IV)                                  (V)

wherein $R^1$, $R^2$, $R^3$, $R^4$, n and m have the same meaning as previously defined, and X is chloro or bromo.

The acylation reaction (2) is conducted by conventional procedures. The reactants (IV) and (V) are generally contacted in substantially equimolar amounts in an inert organic solvent at a temperature of 0° to 100° C. Suitable inert organic solvents include ethyl acetate, dichloromethane, dimethoxymethane, benzene, etc. If desired, a base such as a trialkylamine or a pyridine compound may be employed to scavenge the hydrogen halide by-product. The product (II) is isolated and purified by conventional procedures such as extraction, distillation, chromatography, crystallization, etc.

The carbonyl compound (IV) is prepared by a variety of methods. One method for preparing compounds of formula (IV) is depicted in the following reaction (3):

$$\text{ArNH}_2 + X-(\underset{R^2}{\underset{|}{C}})_m-(CH_2)_n-\underset{R^3}{\underset{|}{C}}=O \longrightarrow (IV) + HX \quad (3)$$

(VI)                    (VII)

wherein Ar, $R^2$, $R^3$, $R^4$, X, m and n have the same meaning as previously defined.

Reaction (3) is the alkylation of an aniline compound (VI) with an alpha-halo or beta-halo carbonyl compound (VII). The alkylation reaction is conducted by more-or-less conventional procedures. For example, the reaction is generally conducted by contacting substantially equimolar amounts of the aniline compound (VI) and the alpha-halo or beta-halo carbonyl compound (VII) in the liquid phase in an inert organic diluent at a temperature of 25° C. to 150° C. Reaction (3) is preferably conducted with an alpha-bromo carbonyl compound.

A method of preparing anilino-carbonyl compounds of formula (II) wherein n is zero comprises the reaction of an aniline compound (VI) with an alpha-hydroxy carbonyl compound to give the carbonyl compound (IX), as depicted in the following reaction (4):

$$\text{ArNH}_2 + R^2-\overset{O}{\underset{\|}{C}}-\underset{}{\overset{OH}{\underset{|}{CH}}}-R^3 \longrightarrow \text{ArNH}-CH-\underset{R^3}{\underset{|}{C}}=O + H_2O \quad (4)$$

(VI)        (VIII)                                $R^2$ (IX)

wherein Ar, $R^2$ and $R^3$ have the same meaning as previously defined.

Reaction (4) is conducted by reacting substantially equimolar amounts of the aniline compound (VI) and alpha-hydroxy carbonyl compound (VIII) in the liquid phase in an inert diluent at a temperature of 25° to 150° C. Water is a by-product of the reaction, and the reaction is generally driven to completion by removing the water as it is formed in the reaction, for example as an azeotropic distillation with benzene. Reaction (4) is preferably conducted with alpha-hydroxy ketones, e.g., compounds of formula (VIII) wherein $R^2$ is alkyl or aryl. Most preferably, the reaction is conducted with compounds of formula (VIII) wherein both $R^2$ and $R^3$ are alkyl.

Another method of preparing compounds of formula (II) wherein n is zero is depicted by the following reaction sequence (5):

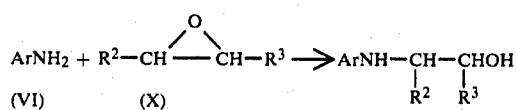 (5a)

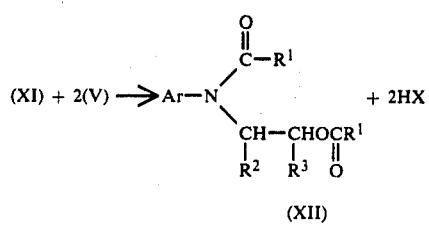 (5b)

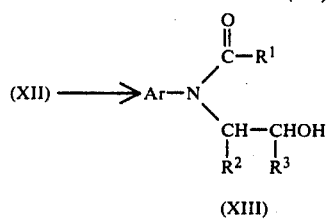 (5c)

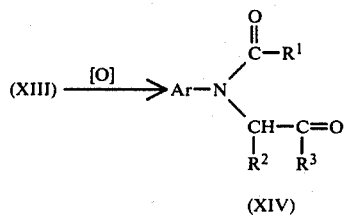 (5d)

wherein Ar, $R^1$, $R^2$, $R^3$ and X have the same meaning as previously defined.

Reaction (5a) comprises the reaction of the aniline compound (VI) with an epoxide (X) to give the anilino-alcohol (XI). The reaction of the aniline compound (VI) and the epoxide (X) is conducted by contacting substantially equimolar amounts of the reactants in the liquid phase, generally in an inert diluent, at a temperature of 0° C. to 100° C. until the reaction is complete. Reaction 5(b) comprises the bis-acylation of the anilino-alcohol to give the acetanilide-ester (XII) by conventional procedures. Reaction (5c) comprises the cleavage of the ester group of the acetanilide ester (XII) to give the hydroxy acetanilide compound (XIII). Reaction (5d) comprises the oxidation of the hydroxy acetanilide compound (XIII) to the carbonyl compound (XIV) with conventional oxidizing agents, e.g., potassium permanganate, chromium trioxide in pyridine, etc.

An alternate method of making compounds of the invention, particularly wherein R is other than hydrogen or alkyl, is to make the oxime (XV) or acylated oxime (XVI) as shown below under the general conditions described above for reaction (1):

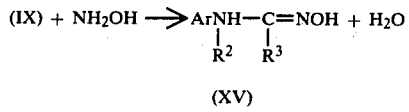 (6)

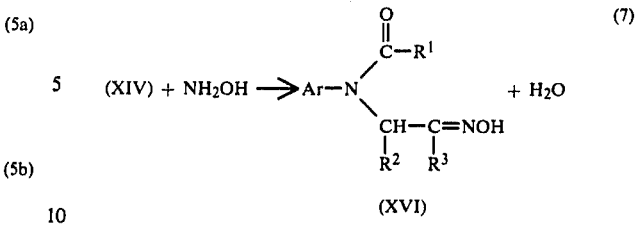 (7)

By conventional procedures, the acylated oxime (XVI) can be reacted with reagents such as phenylisocyanate, methylisocyanate, benzyl bromide, allyl bromide, etc., to directly yield compounds of the invention wherein R is $$\phi NH\overset{O}{\underset{\|}{C}}-,\ CH_3NH\overset{O}{\underset{\|}{C}}-,\ \phi CH_2-,\ CH_2=CH-CH_2,$$

respectively. Alternatively, these reagents can be reacted with the oxime (XV), followed by acylation according to the general conditions described above for reaction (2).

The preferred procedure for making compounds of the invention wherein $R^3$ is methyl, m=0 and n=1 is as follows:

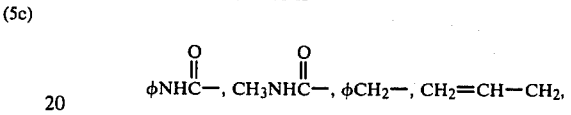 (8)

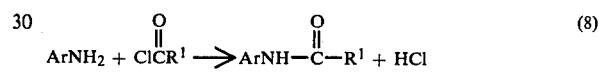 (9)

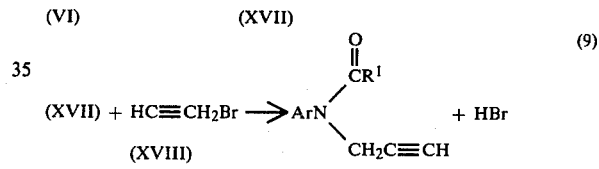

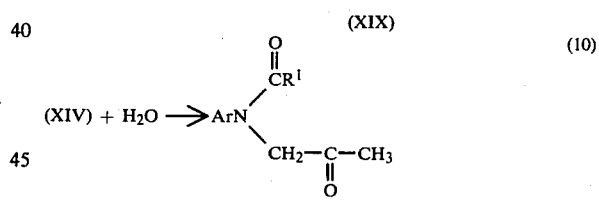 (10)

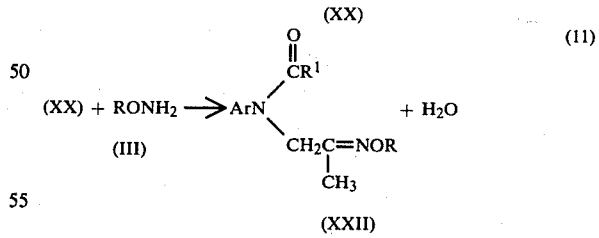 (11)

Reaction (8) is a conventional acylation and can be carried out under conditions described for reaction (2) described above. Reaction (9) can be carried out by reacting substantially equimolar amounts of the amide (XVII) with propargyl bromide (XVIII) in aqueous solution in the presence of a base scavenger and a phase-transfer catalyst, such as tetrabutyl ammonium bromide, at ambient temperature. The hydration reaction (10) can be carried out in an aqueous acidic organic solvent, such as aqueous formic acid, in the presence of a catalyst, such as mercuric oxide. Reaction (11) is a conventional oxime formation and can be conducted under conditions described above for reaction (1).

EXAMPLES

Example 1—Preparation of 2-(2,6-dimethylphenylamino)cyclopentanol

A solution of 8.4 g (0.1 mol) cyclopentane-1,2-oxide and 12.1 g (0.1 mol) 2,6-dimethylaniline in 100 ml toluene was mixed with 6 drops of boron trifluoride etherate. The solution was heated under reflux for 2 hours and then evaporated under reduced pressure to give an oil residue. The residue was chromatographed on 120 g of silica gel using successively as eluant 1 liter dichloromethane, 1 liter 5% acetone in dichloromethane and 1 liter 10% acetone in dichloromethane. 2-(2,6-dimethylphenylamino)cyclopentanol (11 g) was the second material eluted. Elemental analysis of this product (a pale yellow oil) for $C_{13}H_{19}NO$ showed:

|     | Calc. | Found |
| --- | --- | --- |
| % C | 76.1 | 76.5 |
| % H | 9.3  | 9.9  |
| % N | 6.8  | 6.4  |

Example 2—Preparation of 2-(N-chloroacetyl-2,6-dimethylphenylamino)cyclopentanone A solution of 7.1 g (0.035 mol) 2-(2,6-dimethylphenylamino)cyclopentanol and 9.4 g (0.083 mol) chloroacetyl chloride in about 200 ml toluene was stirred at about 25° C. for 20 hours and then heated under reflux for 1.5 hours. The reaction mixture was cooled and evaporated under reduced pressure to give an amber oil. The oil was chromatographed on 60 g silica gel using ethyl ether. The eluted oil product (7.4 g) crystallized on standing. Recrystallization from ethyl ether/hexane gave 1-chloroacetoxy-2-(N-chloroacetyl-2,6-dimethylphenylamino)cyclopentane, as a white solid, m.p. 96°–98° C. Elemental analysis for $C_{17}H_{21}Cl_2NO_3$ showed: %Cl, calc. 19.8, found 19.7.

A slurry of 5 g of 1-chloroacetoxy-2-(N-chloroacetyl-2,6-dimethylphenylamino)cyclopentane and 1 g of potassium carbonate in 100 ml ethanol was stirred at 0°–10° C. (ice bath) for 2 hours. The reaction mixture was then filtered and evaporated under reduced pressure to give an oily residue. The residue was taken up in ethyl ether, washed with water, dried over magnesium sulfate and evaporated under reduced pressure to give 4 g of 2-(N-chloroacetyl-2,6-dimethylphenylamino)cyclopentanol, as a pale amber oil. Elemental analysis for $C_{15}H_{20}ClNO_2$ showed: %Cl, calc. 12.6, found 12.9.

A 4.5-ml (0.004-mol) sample of Jones Reagent (26.72 g chromium trioxide in 23 ml of concentrated sulfuric acid diluted with $H_2O$ to 100 ml) was added dropwise to a vigorously stirred solution of 4.4 g (0.016 mol) 2-(N-chloroacetyl-2,6-dimethylphenylamino)cyclopentanol in 100 ml acetone. The acetone solution was decanted from the solids, dried over magnesium sulfate, treated with silica and evaporated under reduced pressure to give 3.7 g of pale yellow oil. The oil was chromatographed on silica gel using mixtures of ethyl ether/hexane as eluant. 2-(N-chloroacetyl-2,6-dimethylphenylamino)cyclopentanone was eluted with 25% ethyl ether/hexane, as a white solid. This product melted at 79°–82° C. after recrystallization from hexane. This product is tabulated in Table I, as Compound No. 1-A.

Example 3—Preparation of 2-(N-chloroacetyl-2,6-dimethylphenylamino)cyclopentanone O-methyloxime A solution of 3 g (0.01 mol) 2-(N-chloroacetyl-2,6-dimethylphenylamino)cyclopentanone, 1.5 g (0.015 mol) triethylamine and 1.25 g (0.015 mol) methoxyamine hydrochloride in 75 ml ethanol was treated under reflux for 16 hours. After standing at room temperature for 4 days, the reaction mixture evaporated under reduced pressure to give a solid residue. The solid was partitioned between dichloromethane and water. The water layer was extracted with dichloromethane and the combined dichloromethane solutions were dried over magnesium sulfate and evaporated under reduced pressure to give a brown oil. The oil was crystallized from ethyl ether/hexane to give 0.57 g of 2,6-dimethyl-alpha-chloroacetanilide as a by-product. The mother liquor was concentrated and chromatographed on silica gel using dichloromethane as an eluant. The eluted material (1.7 g) crystallized on standing to give the desired O-methyloxime product as a white solid, m.p. 57°–59° C. This product is tabulated in Table I as Compound No. 1-B.

Example 4—Preparation of 3-(N-chloroacetyl 2,6-dimethylphenylamino)-2-butanone A mixture of 121 g (1 mol) dimethylaniline, 149 g (1 mol) 3-bromo-2-butanone and 126 g (1.5 mol) sodium bicarbonate in 500 ml ethanol was stirred at 60°–70° C. for about 18 hours. The reaction mixture was filtered and the filtrate evaporated under reduced pressure to give an oil. The oil was taken up in dichloromethane, dried over magnesium sulfate, treated with silica, filtered and evaporated under reduced pressure to give 174.8 g of 3-(2,6-dimethylphenylamino)-2-butanone as a light amber oil. The infrared spectrum of the product showed strong carbonyl absorption at 5.8 microns.

A 152.6-g (1.35-mol) sample of chloroacetyl chloride was added over 0.25 hour in small portions to a stirred solution of 170.8 g (0.89 mol) 3-(2,6-dimethylphenylamino)-2-butanone in 500 ml toluene. The reaction mixture was heated under reflux for 3 hours, cooled and filtered. The filtrate was concentrated and chromatographed on silica gel using dichloromethane eluant. The eluted material was recrystallized several times from ethyl ether/hexane to give the 3-(N-chloroacetyl-2,6-dimethylphenylamino)-2-butanone product, as a brown solid, m.p. 78°–82° C. The infrared spectrum of the product showed strong carbonyl absorption at 5.8 and 6.1 microns. This product is tabulated in Table I as Compound No. 5-A.

Example 5—Preparation of 3-(N-chloroacetyl-2,6-dimethylphenylamino)-2-butanone O-methyloxime To 10 g (0.037 mol) 3-(N-chloroacetyl-2,6-dimethylphenylamino)-2-butanone in 75 ml ethanol were added 6.2 g methoxyamine hydrochloride, 10.2 g potassium carbonate and 20 cc 4-Angstrom molecular sieves. The resulting mixture was allowed to stir at 25° C. for about 18 hours. The mixture was filtered and evaporated under reduced pressure to give 7.5 g of an oil. The oil was taken up in ethyl ether and cooled to crystallize out 1.8 g of 3-(N-chloroacetyl-2,6-dimethylphenylamino)-2-butanone. Hexane was added to the mother liquor and cooling crystallized out an additional 1.5 g of 3-(N-chloroacetyl-2,6-dimethylphenylamino)-2-butanone. The mother liquor was then evaporated under reduced pressure to give 4.4 g of 3-(N-chloroacetyl-2,6-dimethylphenylamino)-2-butanone O-methyloxime, as an oil. The infrared spectrum of the product showed carbonyl absorption at 5.95 micron and a strong absorption at 9.6 micron. This product is tabulated in Table I as Compound No. 5-B.

Example 6—Preparation of alpha-(N-chloroacetyl-2,6-dimethylphenylamino)acetaldehyde A solution of 2 g alpha-(N-chloroacetyl-2,6-dimethylphenylamino)acetaldehyde diethylacetal (U.S. Pat. No. 3,966,811) and 0.1 g p-toluenesulfonic acid in 50 ml acetone was heated under reflux for 3 hours. The reaction mixture was evaporated under reduced pressure, diluted with ethyl ether, washed with water, washed with sodium bicarbonate solution and evaporated to an oil. Analysis of the oil indicated the presence of about 50% of the starting diethylacetal.

The oil, 3 g of additional diethylacetal and 0.3 g of additional p-toluenesulfonic acid in 50 ml acetone were heated under reflux for 10 hours. The reaction mixture was worked up as described above to give an oil. The oil was chromatographed through a silica gel column. The desired product (2.6 g) was eluted with 10% ethyl ether in hexane. The infrared spectrum of the product showed strong carbonyl absorption at 5.8 micron and 6.0 micron. The product is tabulated in Table I as Compound No. 8-A.

Example 7—Preparation of alpha-(N-chloroacetyl-2-methyl-6-ethylphenylamino)acetaldehyde oxime A solution of 5 g (0.2 mol) alpha-(N-chloroacetyl-2-methyl-6-ethylphenylamino)acetaldehyde, 3.3 g (0.04 mol) hydroxylamine hydrochloride and 3.4 g (0.04 mol) sodium bicarbonate in 50 ml ethanol was heated at 40° C. for 40 minutes. The reaction mixture was filtered, evaporated under reduced pressure, diluted with ethyl ether, filtered again and evaporated under reduced pressure to give 5.5 g of a yellow oil which crystallized to a solid on standing. The crude solid was recrystallized from ethyl ether/hexane to give 3.2 g of the product as a white solid, m.p. 113°–115° C. The product is tabulated in Table I as Compound No. 12.

Example 8—Preparation of beta-(N-chloroacetyl-2,6-dimethylphenylamino)propionaldehyde A solution of 33.9 g (0.28 mol) dimethylaniline, 50 g (0.3 mol) beta-chloropropionaldehyde diethylacetal, 45 g (0.3 mol) sodium iodide and 48.3 g (0.35 mol) potassium bicarbonate in 300 ml ethanol was heated under reflux for 7 hours. The reaction mixture was cooled, filtered and evaporated under reduced pressure to give 28.1 g of an amber oil. The oil was distilled (pot temperature 133°–135° C. at 0.5 mm Hg) to give 16.1 g of beta-(2,6-dimethylphenylamino)propionaldehyde diethylacetal.

An 8.6-g (0.076-mol) sample of chloroacetyl chloride was added dropwise to a solution of 16 g (0.06 mol) beta-2,6-dimethylphenylamino)propionaldehyde diethylacetal and 6 g (0.076 mol) pyridine in 60 ml ethyl acetate. A salt immediately precipitated. The reaction mixture was stirred at about 25° C. for about 18 hours. The reaction mixture was filtered and the filtrate was evaporated under reduced pressure to give an oil. The oil was mixed with 100 ml acetone, 25 ml water and about 0.5 g p-toluenesulfonic acid. The resulting solution was stirred for 2 hours at 25° C., diluted with water, and extracted with ethyl ether. The ether extracts were evaporated to give a pale yellow oil. The yellow oil was dissolved in dichloromethane, dried over magnesium sulfate, treated with silica, filtered and evaporated to give 12.3 g of an oil which partially crystallized to give the product. Infrared analysis showed amide carbonyl absorption at 6.0 micron and aldehyde carbonyl absorption at 5.8 micron. The product is tabulated in Table I as Compound No. 13-A.

Example 9—Preparation of beta-(N-chloroacetyl-2,6-dimethylphenylamino)propionaldehyde O-methyloxime A 2.0-g (0.024-mol) sample of methoxyamine hydrochloride was added slowly to a slurry of 3.0 g (0.012 mol) beta-(N-chloroacetyl-2,6-dimethylphenylamino)-propionaldehyde and 2.0 g (0.02 mol) sodium bicarbonate in 75 ml ethanol. The reaction mixture was stirred at about 35° C. for 2 hours, filtered and evaporated to give 2.9 g of the product as an oil. The product is tabulated in Table I as Compound No. 13-B.

Example 10—Preparation of 3-(N-chloroacetyl-2,6-dimethylphenylamino)-butan-2-one O-methyloxime A solution of 484.8 g (4 mols) 2,6-dimethylaniline and 422.8 g (4.8 mols) 3-hydroxy-2-butanone in 1200 ml benzene was heated under reflux for 21 hours in a reaction vessel equipped with a Dean-Stark trap. The reaction mixture was then cooled, washed with four 600-ml portions of water, slurried with silica gel, filtered and evaporated under reduced pressure to give 722 g of 3-(2,6-dimethylphenylamino)-2-butanone, as an orange oil. The infrared spectrum of the product showed strong carbonyl absorption at 6.3 microns.

A sample of 50.5 g triethylamine was added dropwise to a solution of 50.1 g (0.6 mol) methoxyamine hydrochloride in 75 ml dichloromethane at 9°–20° C. To the resulting solution was added about one-half of a 95.6-g (0.5-mol) sample of 3-(2,6-dimethylphenylamino)-2-butanone. The reaction temperature rose from 16° C. to 30° C. The reaction mixture was cooled in an ice bath, and the remaining 3-(2,6-dimethylphenylamino)-2-butanone was added dropwise. The reaction mixture was then stirred about 18 hours at about 20° C., washed with 50 ml of water and evaporrated under reduced pressure to give 100.3 g of 3-(2,6-dimethylphenylamino)-2-butanone O-methyloxime, as an oil. The nuclear magnetic resonance spectrum showed a sharp 3-proton singlet (—OCH$_3$) at 3.9 ppm (relative to tetramethylsilane) and a sharp 6-proton singlet (2,6-dimethyl groups) at 2.2 ppm.

A sample of 54.2 g (0.048 mol) chloroacetyl chloride and a sample of 34.8 g (0.44 mol) pyridine was added over a 25-minute period to a solution of 97.0 g (0.44 mol) 3-(2,6-dimethylphenylamino)-2-butanone O-methyloxime maintained at 45° C. in 500 ml benzene. The pyridine was added slightly faster than the chloroacetyl chloride. The reaction temperature rose to about 50°–58° C. during the addition. The reaction mixture was then cooled, washed with water, washed with 5% aqueous sodium bicarbonate solution, stirred with silica gel, filtered and evaporated under reduced pressure to give 111.5 g of 3-(N-chloroacetyl-2,6-dimethylphenylamino)-2-butanone O-methyloxime, as an oil. The infrared spectrum of the product showed carbonyl absorption at 5.9 micron and O—CH3 absorption at 9.5 micron. The product is tabulated in Table I as Compound No. 5-B.

Example 11—Preparation of 3-(N-chloroacetyl-2,6-dimethylphenylamino)-2-butanone O-methylcarbamyl oxime 3-(N-chloroacetyl-2,6-dimethylphenylamino)-2-butanone oxide (2.6 g) was dissolved in 75 ml methylene chloride and 5 drops of triethylamine were added. To this mixture was added 2.6 g methylisocyanate and the solution was stirred at room temperature. The solution was refluxed for 5 hours and solvent was stripped. The oil was crystallized in ethanol-water to yield 3 g tan product. This product is tabulated as Compound No. 17 in Table I.

Example 12—Preparation of 3-(N-chloroacetyl-2,6-dimethylphenylamino)-2-butanone-O-phenylcarbamyl oxime Following the procedure of Example 11, 3 g of 3-(N-chloroacetyl-2,6-dimethylphenylamino)-2-butanone oxime, 3 g phenylisocyanate and 5 drops triethylamine in 100 ml methylene chloride were stirred, refluxed and worked up to yield the title product, m.p. 115°–117° C. This product is tabulated as Compound No. 18 in Table I.

Example 13—Preparation of 3-(N-chloroacetyl-2,6-dimethylphenylamino)-2-butanone O-benzyl oxime To a solution of 5.4 g of 3-(2,6-dimethylphenylamino)-2-butanone O-benzyl oxime and 1.6 g pyridine in 100 ml ethyl acetate was added dropwise over 10 minutes 2.3 g chloroacetyl chloride. The solution was stirred for an additional 30 minutes at room temperature and poured into 1 liter of water. The mixture was extracted with methylene chloride (4×75 ml). The extracts were dried (MgSO4), purified on silica gel, stripped of solvent to yield 6.3 g light amber oil. The oil was centrifuged and the 5.7 g of the title product was pipetted from the tube. This product is tabulated as Compound No. 19 in Table I.

Example 14—Preparation of 3-(N-chloroacetyl-2,6-dimethylphenylamino)-2-butanone O-allyl oxime To a solution of 3-(2,6-dimethylphenylamino)-2-butanone O-allyl oxime (4.5 g) in 75 ml ethyl acetate and 1.6 g pyridine was added dropwise 2.3 g chloroacetyl chloride. The mixture was stirred for 15 minutes, and poured into 1 liter of water. The organic phase was collected, diluted with 100 ml ether, washed with water, dried (MgSO4), treated with silica gel and stripped of solvent to yield 4.9 g yellow oil. The oil was chromatographed on silica gel (125 g) with elution by 3:1 CH2Cl2:hexane followed by 5% acetone:CH2Cl2, to yield 2.5 g of the title product. This compound is tabulated as Compound No. 20 in Table I.

Example 15—Preparation of 3-(N-chloroacetyl-2,6-dimethylphenylamino)-1-methyoxypropan-2-one O-methyl oxime 3-(N-chloroacetyl-2,6-dimethylphenylamino)-1-methoxypropan-2-one (3.0 g) was dissolved in 50 ml dry ethanol and methoxyamine hydrochloride (1.25 g) and potassium carbonate (2.1 g) were added. The mixture was stirred overnight at room temperature, warmed on a water bath for 10 minutes and poured into 500 ml water. Extraction with methylene chloride followed by drying (MgSO4) and stripping of the solvent yielded 3.0 g of colorless oil, the title compound. This compound is tabulated as Compound No. 21 in Table I.

The compounds tabulated in Table I were prepared by procedures similar to those of Examples 1–15. The structure of each compound tabulated in Table I was confirmed by nuclear magnetic resonance and/or infrared spectroscopy.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The oxime compounds are particularly effective as pre-emergent herbicides against weed grasses.

The oxime compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The oxime compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of oxime compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent herbicidal control, the compounds of the invention are applied at rates of 0.2 to 60 kg/ha, and the preferred rate is in the range 0.5 to 40 kg/ha. For plant growth regulating or retarding activity, it is essential to apply the oxime compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal and plant-growth-regulating tests on representative compounds of the invention were made using the following methods.

Pre-Emergent Herbicidal Test

An acetone solution of the test compound was prepared by mixing 375 mg of the compound, 118 mg of a non-ionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

AXILLARY BUD GROWTH INHIBITION OF PINTO BEAN PLANTS

Compound Nos. 1-B and 5-B were tested to determine their plant-growth-retarding effects on axillary bud growth of pinto beans.

Idaho pinto bean plants (13-16 days old) having monofoliate leaves fully developed and first trifoliates beginning to unfold were used. All growth 5 mm above the monofoliate leaf node was removed with forceps 1 to 4 hours prior to treatment with the test compounds. Four plants were used for each test compound.

A 625-ppm solution of the test compound in a 2% aqueous acetone solution containing a small amount of a non-ionic surfactant was sprayed onto the pinto bean plants until runoff. After drying, the treated plants were transferred to a greenhouse maintained at 20°-23° C. and watered at regular intervals. Twelve days after treatment, the bud growth at the axil of the monofoliate leaf was determined and expressed as percent inhibition of axillary bud growth as compared to untreated check plants. The results are reported in Table III.

AXILLARY BUD GROWTH INHIBITION OF TOBACCO

Compound Nos. 1-B and 5-B were tested to determine their plant-growth-regulating effects on axillary bud growth of tobacco.

Tobacco plants (9-10 weeks old, Glurk cultivar), with their top 15 cm cut off 24 hours before treatment, were used. Three plants were used for each test compound.

A 5% solution of the test compound and a small amount of a non-ionic surfactant were diluted with water to give a 400-ppm test solution. The tobacco plants were sprayed with the test solution until runoff. The plants were then incubated in a greenhouse maintained between 20°-23° C. and watered at regular intervals. After 18-28 days, the percent bud inhibition was determined by comparing the axillary buds at the top three nodes of each plant with those of untreated check plants. The results are tabulated in Table III.

TABLE I

Compounds of the formula $$\begin{array}{c} O \\ \parallel \\ Ar-N \begin{array}{c} C-CH_2Cl \\ \\ CH-(CH_2)_n-C=Y \\ | \qquad\qquad\qquad | \\ R^2 \qquad\qquad\qquad R^3 \end{array} \end{array}$$

| No. | Ar | Y | $R^2$ | $R^3$ | n | m.p., °C. | C Calc. | C Found | H Calc. | H Found | N(Cl) Calc. | N(Cl) Found |
|---|---|---|---|---|---|---|---|---|---|---|---|---|
| 1A | 2,6-(CH$_3$)$_2$—φ | =O | —CH$_2$CH$_2$CH$_2$— | | 0 | 79–82 | | | | | (12.7) | (13.5) |
| 1B | 2,6-(CH$_3$)$_2$—φ | =NOCH$_3$ | —CH$_2$CH$_2$CH$_2$— | | 0 | oil | | | | | (11.5) | (12.1) |
| 2 | 2,6-(CH$_3$)$_2$—φ | =NOC$_2$H$_5$ | —CH$_2$CH$_2$CH$_2$— | | 0 | oil | 63.1 | 62.5 | 7.4 | 7.0 | 8.7 | 8.3 |
| 3 | 2,3-(CH$_3$)$_2$—φ | =NOCH$_3$ | —CH$_2$CH$_2$CH$_2$— | | 0 | oil | 62.1 | 61.9 | 6.9 | 7.0 | 9.1 | 8.9 |
| 4 | 2,6-(C$_2$H$_5$)$_2$—φ | =NOCH$_3$ | —CH$_2$CH$_2$CH$_2$— | | 0 | oil | 64.1 | 59.0 | 7.5 | 7.2 | 8.3 | 8.0 |
| 5A | 2,6-(CH$_3$)$_2$—φ | =O | CH$_3$ | CH$_3$ | 0 | 78–82 | 62.8 | 64.2 | 6.7 | 6.9 | 5.2 | 5.4 |
| 5B | 2,6-(CH$_3$)$_2$—φ | =NOCH$_3$ | CH$_3$ | CH$_3$ | 0 | oil | 60.6 | 60.4 | 7.1 | 7.0 | 9.4 | 8.8 |
| 6 | 2-CH$_2$-6-C$_2$H$_5$—φ | =NOCH$_3$ | —CH$_2$CH$_2$CH$_2$— | | 0 | oil | 63.2 | 67.2 | 7.2 | 7.5 | 8.7 | 8.0 |
| 7A | 2,6-(CH$_3$)$_2$—φ | =O | —(CH$_2$)$_4$— | | 0 | 110–112 | | | | | (11.5) | (11.0) |
| 7B | 2,6-(CH$_3$)$_2$—φ | =NOCH$_3$ | —(CH$_2$)$_4$— | | 0 | oil | 63.2 | 60.7 | 7.2 | 7.5 | 8.7 | 5.4 |
| 8A | 2,6-(C$_2$H$_5$)$_2$—φ | =O | CH$_3$ | CH$_3$ | 0 | oil | 65.0 | 64.7 | 7.5 | 7.6 | 4.7 | 4.7 |
| 8B | 2,6-(C$_2$H$_5$)$_2$—φ | =NOCH$_3$ | CH$_3$ | CH$_3$ | 0 | oil | 62.9 | 67.1 | 7.7 | 8.0 | 8.6 | 7.9 |
| 9A | 2,6-(CH$_3$)$_2$—φ | =NOCH$_3$ | H | H | 0 | oil | | | | | (14.8) | (15.6) |
| 9B | 2,6-(CH$_3$)$_2$—φ | =O | H | H | 0 | 55–57 | 58.1 | 59.1 | 6.3 | 6.5 | 10.4 | 10.6 |
| 10 | 2,6-(CH$_3$)$_2$—φ | =NOCH$_3$ | H | H | 0 | oil | 60.7 | 60.6 | 7.4 | 7.4 | 9.4 | 8.5 |
| 11 | 2-CH$_3$-6-C$_2$H$_5$—φ | =NOCH$_3$ | H | H | 0 | oil | 59.5 | 59.1 | 6.7 | 6.7 | 9.9 | 9.5 |
| 12 | 2-CH$_3$-6-C$_2$H$_5$—φ | =NOH | H | H | 0 | 113–115 | 58.1 | 59.8 | 6.3 | 6.8 | 10.4 | 10.9 |
| 13A | 2,6-(CH$_3$)$_2$—φ | =O | H | H | 1 | oil | 61.5 | 59.8 | 6.3 | 6.3 | 5.5 | 5.3 |
| 13B | 2,6-(CH$_3$)$_2$—φ | =NOCH$_3$ | H | H | 1 | oil | 59.5 | 61.6 | 6.7 | 7.0 | 9.9 | 8.6 |
| 14 | 2,6-(CH$_3$)$_2$—φ | =NOCH$_3$ | H | φ | 0 | 77–80 | 66.2 | 67.5 | 6.1 | 6.4 | 8.1 | 8.1 |
| 15A | 2,6-(CH$_3$)$_2$—φ | =O | H | CH$_3$ | 0 | 97–98.5 | | | | | (14.0) | (13.4) |
| 15B | 2,6-(CH$_3$)$_2$—φ | =NOCH$_3$ | H | CH$_3$ | 0 | 59–61 | 59.5 | 59.6 | 6.7 | 6.7 | 9.9 | 9.8 |
| 16A | 2,6-(C$_2$H$_5$)$_2$—φ | =O | H | CH$_3$ | 0 | 65–66 | | | | | (12.6) | (12.6) |
| 16B | 2,6-(C$_2$H$_5$)$_2$—φ | =NOCH$_3$ | H | CH$_3$ | 0 | oil | | | | | (11.4) | (10.9) |
| 17 | 2,6-(CH$_3$)$_2$—φ | (1) | CH$_3$ | CH$_3$ | 0 | 102–114 | 56.6 | 57.6 | 6.5 | 6.6 | 12.4 | 12.0 |
| 18 | 2,6-(CH$_3$)$_2$—φ | (2) | CH$_3$ | CH$_3$ | 0 | 115–117 | 62.8 | 63.3 | 6.0 | 6.4 | 10.5 | 10.5 |
| 19 | 2,6-(CH$_3$)$_2$—φ | =NOCH$_2$φ | CH$_3$ | CH$_3$ | 0 | oil | 67.7 | 64.2 | 6.7 | 6.6 | 7.5 | 7.4 |
| 20 | 2,6-(CH$_3$)$_2$—φ | (3) | CH$_3$ | CH$_3$ | 0 | oil | 63.3 | 64.7 | 7.1 | 7.4 | 8.7 | 9.3 |
| 21 | 2,6-(CH$_3$)$_2$—φ | =NOCH$_3$ | H | (4) | 0 | oil | 57.6 | 58.3 | 6.7 | 7.0 | 9.0 | 8.5 |

(1) $=NOCNHCH_3$ with O above C (2) $=NOCNH\phi$ with O above C (3) =NOCH$_2$CH=CH$_2$ (4) CH$_3$OCH$_2$

TABLE II

Herbicidal Effectivenes
% Control - Pre/Post

| No. | L | M | P | C | W | O |
|---|---|---|---|---|---|---|
| 1A* | 0/0 | 0/0 | 0/0 | 0/0 | 0/0 | 0/0 |
| 1B | 68/35 | 80/25 | 90/30 | 100/65 | 100/80 | 85/20 |
| 2 | 23/— | 7/— | 17/— | 98/— | 100/— | 68/— |
| 3 | 0/— | 0/— | 45/— | 9/— | 99/— | 10/— |
| 4 | 20/— | 0/— | 20/— | 75/— | 98/— | 47/— |
| 5A | 0/0 | 0/0 | 0/0 | 85/0 | 100/0 | 80/0 |
| 5B | 82/— | 47/— | 96/— | 98/— | 100/— | 92/— |
| 6 | 30/— | 0/— | 7/— | 80/— | 99/— | 3/— |
| 7A | 0/0 | 0/0 | 0/0 | 0/0 | 0/0 | 0/0 |
| 7B | 73/— | 0/— | 0/— | 0/— | 10/— | 3/— |
| 8A | 20/0 | 20/0 | 35/0 | 85/40 | 85/60 | 40/25 |
| 8B | 10/40 | 15/20 | 85/40 | 72/75 | 100/80 | 70/55 |
| 9A* | 0/0 | 0/0 | 0/0 | 85/0 | 100/0 | 55/0 |
| 9B | 100/45 | 40/25 | 100/0 | 97/80 | 97/80 | 97/35 |
| 10 | 25/20 | 30/25 | 95/25 | 97/80 | 99/80 | 95/45 |
| 11 | 40/55 | 40/30 | 75/35 | 99/80 | 100/85 | 98/30 |
| 12 | 35/35 | 35/40 | 50/40 | 98/80 | 100/80 | 95/20 |
| 13A | 0/0 | 0/0 | 0/0 | 0/0 | 0/0 | 0/0 |
| 13B | 0/20 | 0/25 | 0/— | 97/80 | 97/80 | 70/25 |
| 14 | 0/0 | 0/0 | 0/0 | 75/10 | 90/70 | 0/25 |
| 15A | 50/0 | 55/0 | 55/0 | 100/0 | 100/0 | 75/0 |
| 16A | 15/0 | 0/0 | 0/0 | 93/20 | —/40 | 80/0 |
| 17 | 0/0 | 0/0 | 0/0 | 93/30 | 95/65 | 0/25 |
| 18 | 0/0 | 0/0 | 0/0 | 97/40 | 95/75 | 35/15 |

TABLE II-continued

Herbicidal Effectivenes
% Control - Pre/Post

| No. | L | M | P | C | W | O |
|---|---|---|---|---|---|---|
| 20 | 15/0 | 15/0 | 45/0 | 95/40 | 95/75 | 93/60 |

*33 micrograms/cm$^2$ dosage.
L = Lambsquarter (*Chenopodium album*)
M = Mustard (*Brassica arvensis*)
P = Pigweed (*Amaranthus retroflexus*)
C = Crabgrass (*Digitaria sanquinalis*)
W = Watergrass (*Echinochloa crusgalli*)
O = Wild Oats (*Avenua fatua*)

TABLE III

| No. | Bud Inhibition Pinto Bean | Tobacco |
|---|---|---|
| 1-B | 75% | 80% |
| 5-B | 58% | 90% |

What is claimed is:
1. A compound of the formula

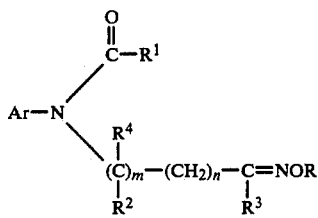

wherein Ar is phenyl or phenyl substituted with 1 to 4 of the same or different substituents selected from fluoro, chloro, bromo, iodo, or alkyl of 1 to 4 carbon atoms, or substituted with 1 to 2 of the same or different substituents selected from alkoxy of 1 to 4 carbon atoms, nitro or haloalkyl of 1 to 2 carbon atoms and 1 to 3 of the same or different halogens selected from fluoro, chloro, bromo or iodo;

$R^1$ is halomethyl of 1 to 3 of the same or different halogens selected from fluoro, chloro, bromo or iodo;

$R^2$ and $R^3$ are each independently hydrogen, alkyl of 1 to 6 carbon atoms, phenyl, benzyl, phenyl or benzyl substituted with 1 to 2 of the same or different substituents selected from fluoro, chloro, bromo, iodo, alkyl of 1 to 4 carbon atoms, alkoxy of 1 to 4 carbon atoms or nitro; haloalkyl of 1 to 4 carbon atoms and 1 to 10 of the same or different halogens selected from fluoro, chloro, bromo or iodo, cyanoalkyl of 2 to 6 carbon atoms, alkoxyalkyl of 2 to 6 carbon atoms, alkylthioalkyl of 2 to 6 carbon atoms, or thiocyanoalkyl of 2 to 6 carbon atoms;

$R^4$ is hydrogen or alkyl of 1 to 6 carbon atoms;

n is 0 or 1;

m is 0 or 1;

R is hydrogen, alkyl of 1 to 6 carbon atoms, alkenyl of 3 to 6 carbon atoms, alkynyl of 3 to 6 carbon atoms, alkylthio of 2 to 6 carbon atoms, haloalkyl of 1 to 4 carbon atoms and 1 to 10 of the same or different halogens selected from fluoro, chloro, bromo or iodo, alkoxyalkyl of 2 to 6 carbon atoms, cyanoalkyl of 2 to 6 carbon atoms, phenyl, benzyl, phenyl or benzyl substituted with 1 to 2 of the same or different substituents selected from fluoro, chloro, bromo, iodo, alkyl of 1 to 4 carbon atoms, alkoxy of 1 to 4 carbon atoms or nitro, or R is acyl of the formula

wherein $R^5$ is hydrogen, alkyl of 1 to 4 carbon atoms, haloalkyl of 1 to 4 carbon atoms and 1 to 10 of the same or different halogens selected from fluoro, bromo, chloro or iodo, alkoxyalkyl of 2 to 6 carbon atoms, alkylthioalkyl of 2 to 6 carbon atoms, alkoxy of 1 to 6 carbon atoms, alkylthio of 1 to 6 carbon atoms, acetonyl, or the group $-NR'R''$ wherein R' and R'' are independently hydrogen, alkyl of 1 to 6 carbon atoms or phenyl.

2. A compound according to claim 1 wherein Ar is phenyl substituted at the 2- and 6-positions.

3. A compound according to claim 2 wherein $R^3$ and R are alkyl, m=0 and n=1.

4. A compound according to claim 2 wherein Ar is 2,6-dialkylphenyl and $R^4$ is hydrogen.

5. A compound according to either Claim 1 or 2 wherein $R^2$ and $R^3$ are each independently hydrogen, alkyl of 1 to 6 carbon atoms, haloalkyl or 1 to 4 carbon atoms and 1 to 10 of the same or different halogens selected from fluoro, bromo, chloro or iodo, cyanoalkyl of 2 to 6 carbon atoms, alkoxyalkyl of 2 to 6 carbon atoms, alkylthioalkyl of 2 to 6 carbon atoms or thiocyanoalkyl of 2 to 6 carbon atoms and m=1.

6. A compound according to claim 4 wherein $R^1$ is monohalomethyl, n=0 and m=1.

7. A compound according to claim 6 wherein R is hydrogen or alkyl of 1 to 6 carbon atoms.

8. A compound according to claim 7 wherein $R^1$ is chloromethyl or bromomethyl and R is alkyl of 1 to 3 carbon atoms.

9. A compound according to claim 8 wherein Ar is 2,6-dimethylphenyl, $R^1$ is chloromethyl, $R^2$ is methyl, $R^3$ is methyl and R is methyl.

10. A compound according to claim 6 wherein $R^2$ is hydrogen.

11. A compound according to claim 6 wherein $R^2$ and $R^3$ are hydrogen.

12. A compound according to claim 11 wherein R is hydrogen or alkyl of 1 to 6 carbon atoms.

13. A compound according to claim 12 wherein Ar is 2,6-dimethylphenyl, $R^1$ is chloromethyl and R is hydrogen or methyl.

14. An herbicidal composition comprising a biologically inert carrier and an herbicidally effective amount of the compound of the formula defined in claim 1.

15. A plant-growth-regulating or retarding composition comprising a biologically inert carrier and a plant-growth-regulating or retarding amount of the compound of the formula defined in claim 1.

16. A method for retarding plant growth which comprises applying to said plants or their growth environment a plant-growth-retarding amount of the compound of the formula defined in claim 1.

17. A method for killing vegetation which comprises applying to said vegetation or its growth environment an herbicidally effective amount of the compound of the formula defined in claim 1.

18. The method of claim 16 wherein Ar is 2,6-dialkylphenyl, $R^1$ is monohalomethyl and n is 0.

19. The method of claim 17 wherein Ar is 2,6-dialkylphenyl, $R^1$ is monohalomethyl and n is 0.

20. A compound according to claim 3 wherein Ar is 2,6-dimethylphenyl, R and $R^3$ are both methyl, and $R^1$ is chloromethyl.

21. A compound according to claim 11 wherein Ar is 2-methyl-6-ethylphenyl, $R^1$ is chloromethyl and R is methyl.

* * * * *